US011857419B2

(12) United States Patent
Szalay

(10) Patent No.: US 11,857,419 B2
(45) Date of Patent: Jan. 2, 2024

(54) METHODS AND APPARATUS FOR FACILITATING GRAFTING IN SURGICAL PROCEDURES

(71) Applicant: Samaritan Biologics, LLC, Cordova, TN (US)

(72) Inventor: David W Szalay, Germantown, TN (US)

(73) Assignee: SAMARITAN BIOLOGICS, LLC, Memphis, TN (US)

( * ) Notice: Subject to any disclaimer, the term of this patent is extended or adjusted under 35 U.S.C. 154(b) by 412 days.

(21) Appl. No.: 16/782,256

(22) Filed: Feb. 5, 2020

(65) Prior Publication Data

US 2020/0268517 A1   Aug. 27, 2020

Related U.S. Application Data

(60) Provisional application No. 62/808,518, filed on Feb. 21, 2019.

(51) Int. Cl.
*A61B 17/86* (2006.01)
*A61B 17/80* (2006.01)
*A61F 2/28* (2006.01)
*A61B 17/70* (2006.01)
*A61F 2/30* (2006.01)
*A61F 2/44* (2006.01)

(52) U.S. Cl.
CPC ............ *A61F 2/28* (2013.01); *A61B 17/8695* (2013.01); *A61F 2/3094* (2013.01); *A61B 17/7032* (2013.01); *A61B 17/8047* (2013.01); *A61F 2/446* (2013.01); *A61F 2002/2835* (2013.01); *A61F 2002/30115* (2013.01); *A61F 2310/00359* (2013.01)

(58) Field of Classification Search
CPC ............ A61B 17/8695; A61B 17/8047; A61B 17/8028; A61B 17/7032; A61B 17/58; A61F 2/0811
See application file for complete search history.

(56) References Cited

U.S. PATENT DOCUMENTS

| | | | | |
|---|---|---|---|---|
| 5,961,521 A | * | 10/1999 | Roger | A61B 17/0642 606/328 |
| 5,968,047 A | * | 10/1999 | Reed | A61B 17/866 606/76 |
| 6,248,108 B1 | * | 6/2001 | Tormala | A61B 17/8625 411/533 |
| 6,309,395 B1 | | 10/2001 | Smith | |
| 7,229,445 B2 | * | 6/2007 | Hayeck | A61B 17/809 606/70 |
| 7,981,156 B2 | | 7/2011 | Pafford | |

(Continued)

*Primary Examiner* — Brian A Dukert
(74) *Attorney, Agent, or Firm* — Matthew B. Dernier, Esq.

(57) ABSTRACT

A graft collar includes a body of cylindrical shape, including an upper surface and a spaced apart lower surface defining an outer wall and surface therebetween; an engagement section located on the upper surface of the body sized and shaped to engage a head of a bone fastener; an through hole extending axially through the body between the upper surface and the lower surface thereof, the through hole being sized to receive therethrough an elongate threaded shank extending from the head of the bone fastener, where the graft collar is formed from at least one of soft cadaveric allograft, hard cadaveric allograft, and synthetic bone void fillers.

19 Claims, 15 Drawing Sheets

(56) References Cited

U.S. PATENT DOCUMENTS

| | | | |
|---|---|---|---|
| 8,197,513 B2* | 6/2012 | Fisher | A61B 17/7064 |
| | | | 606/279 |
| 8,506,608 B2* | 8/2013 | Cerynik | A61B 17/72 |
| | | | 606/76 |
| 9,044,277 B2* | 6/2015 | O'Neil | A61B 17/8038 |
| 9,241,797 B2 | 1/2016 | McKay | |
| 9,622,851 B2 | 4/2017 | Stone | |
| 9,775,723 B2 | 10/2017 | Boyd | |
| 11,246,638 B2* | 2/2022 | Bonutti | A61B 17/7233 |
| 2021/0177466 A1* | 6/2021 | Verlaan | A61K 9/0024 |

* cited by examiner

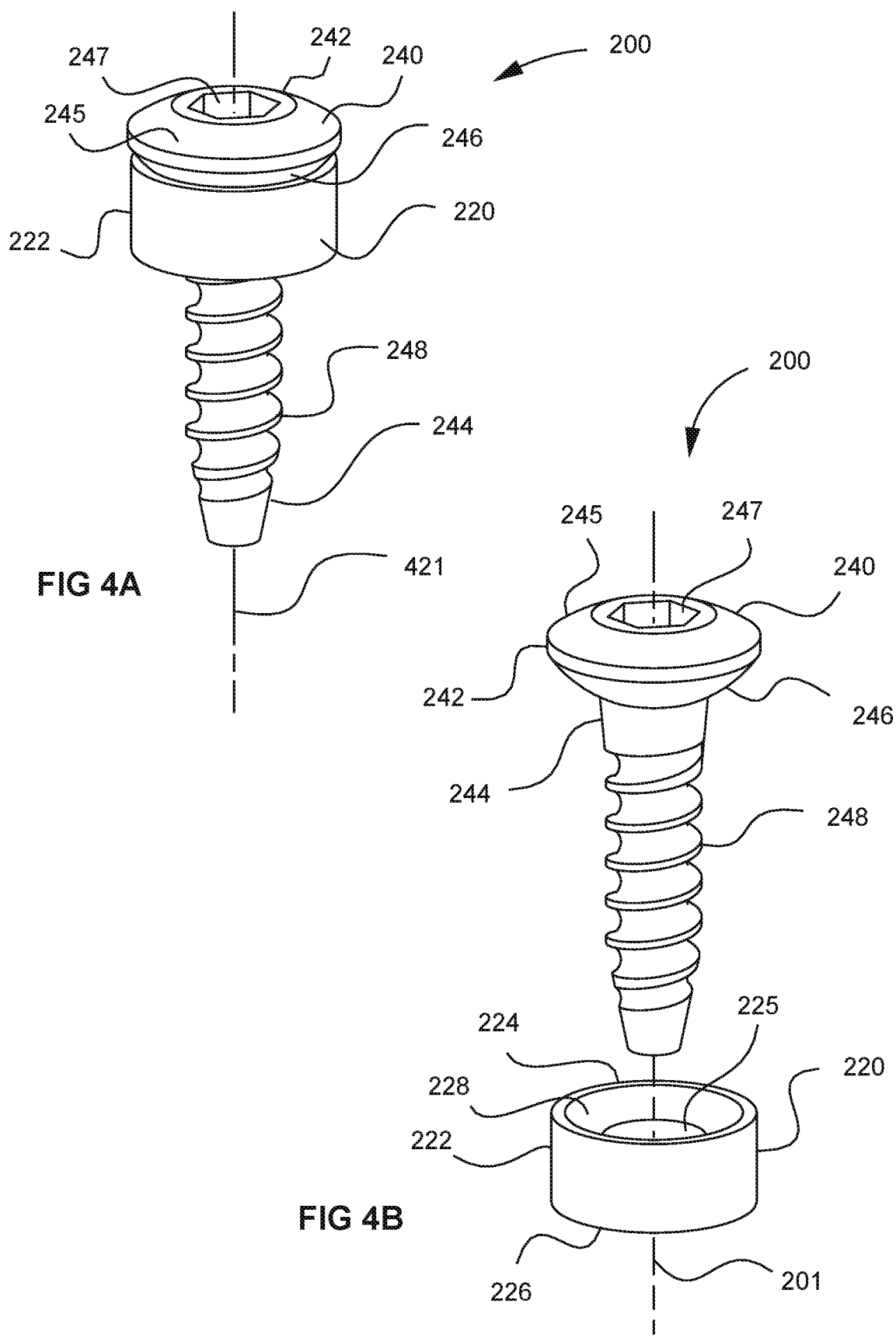

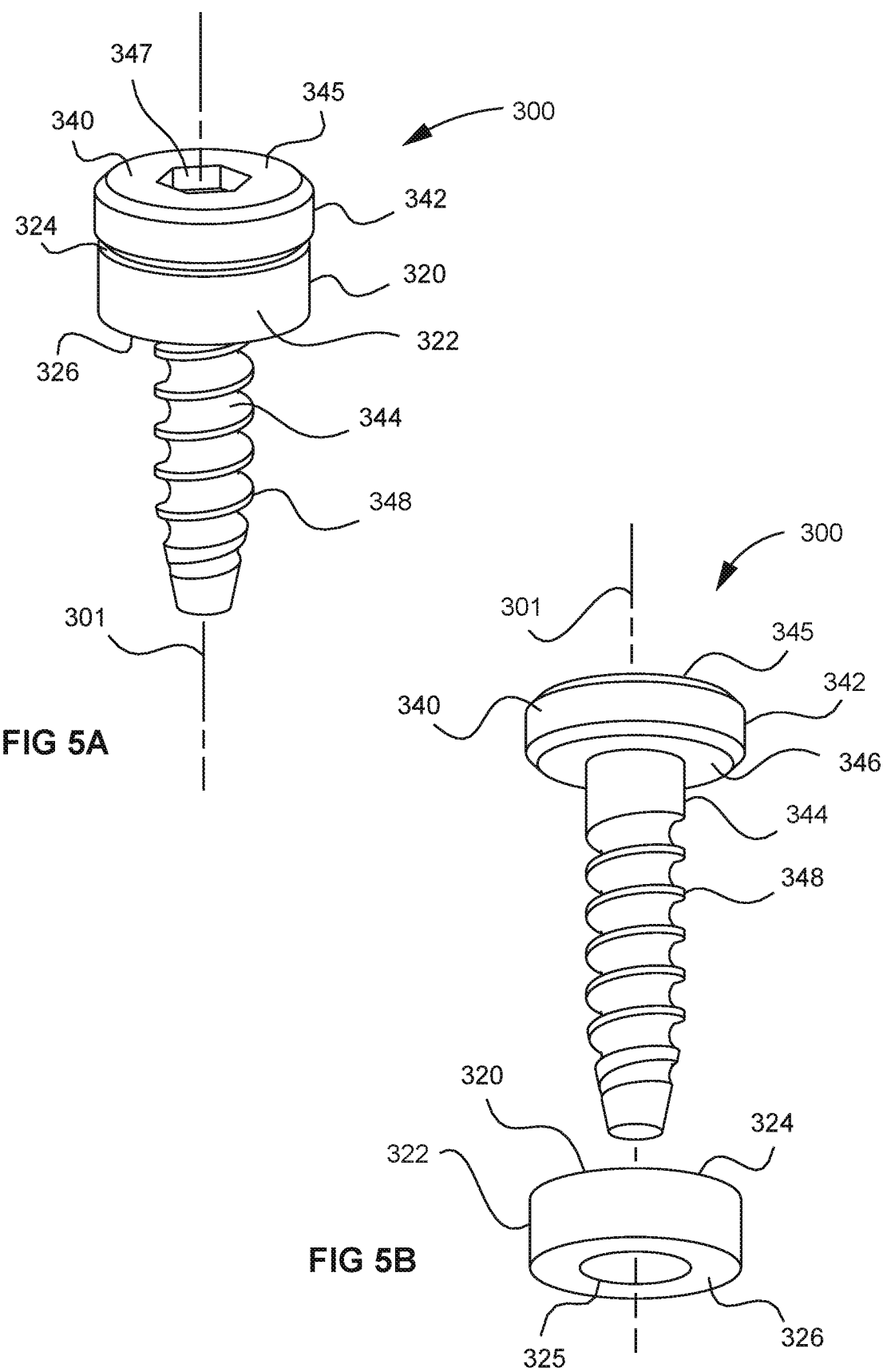

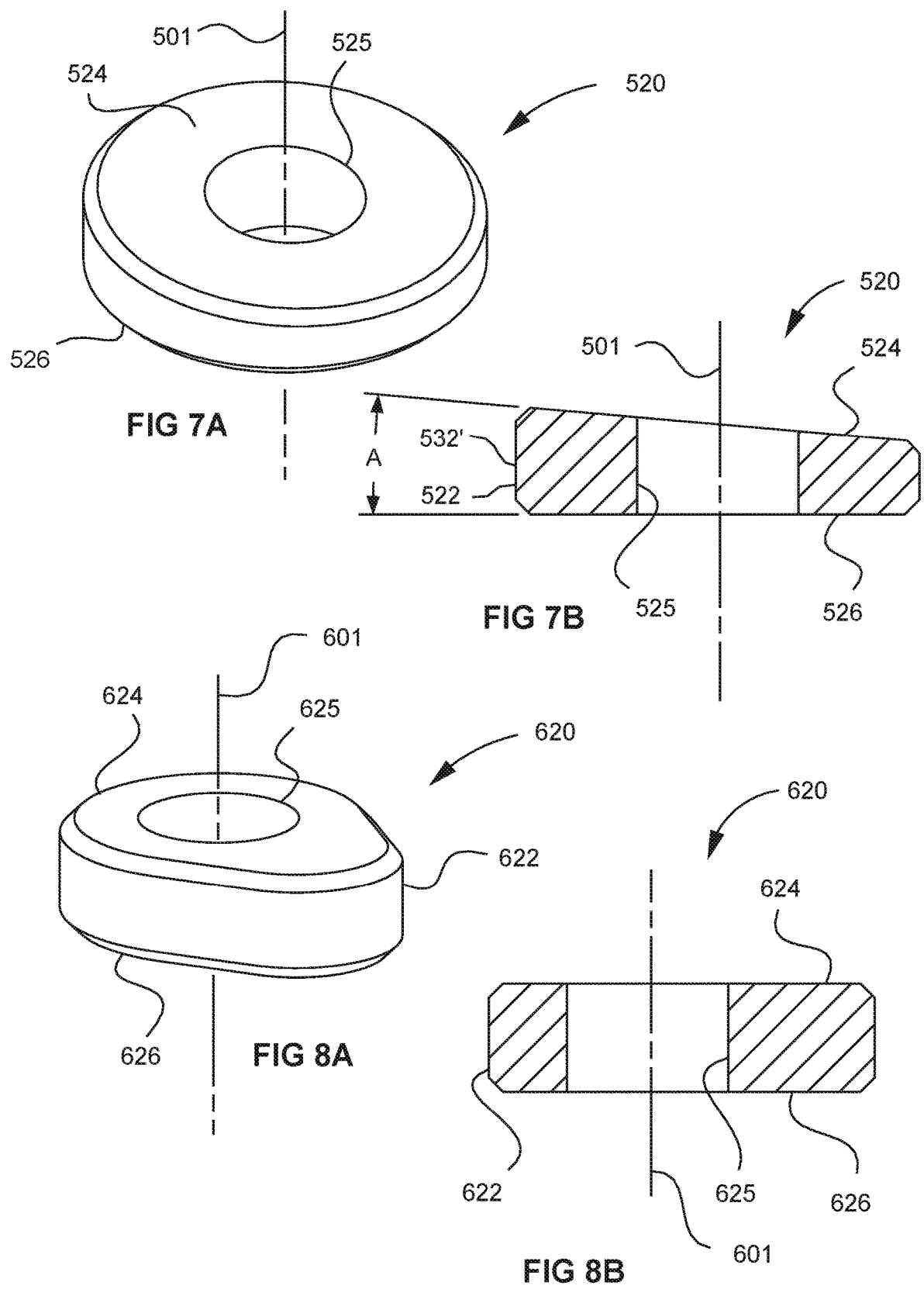

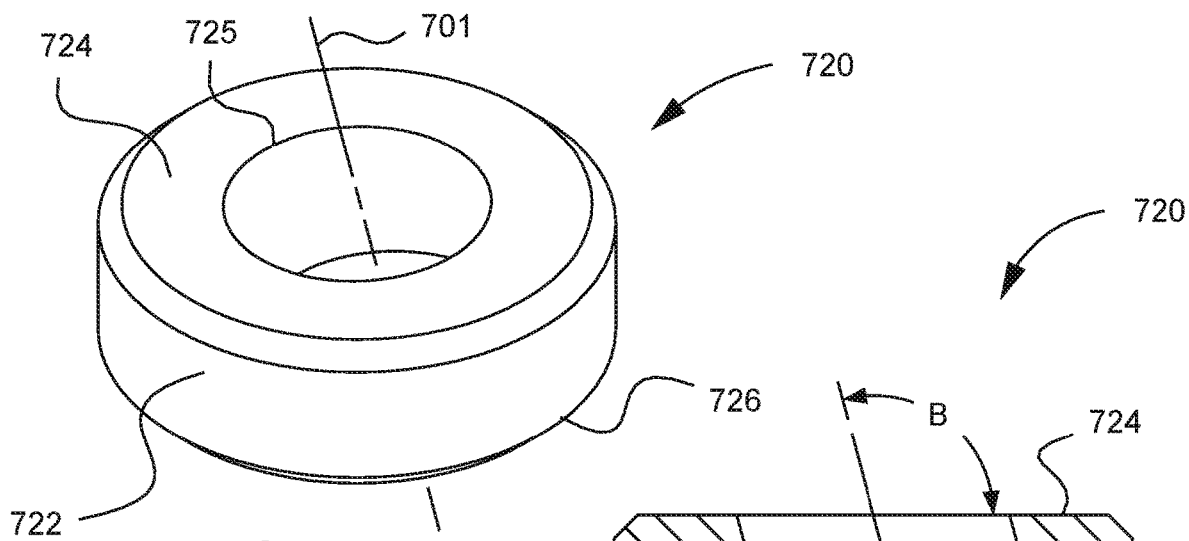
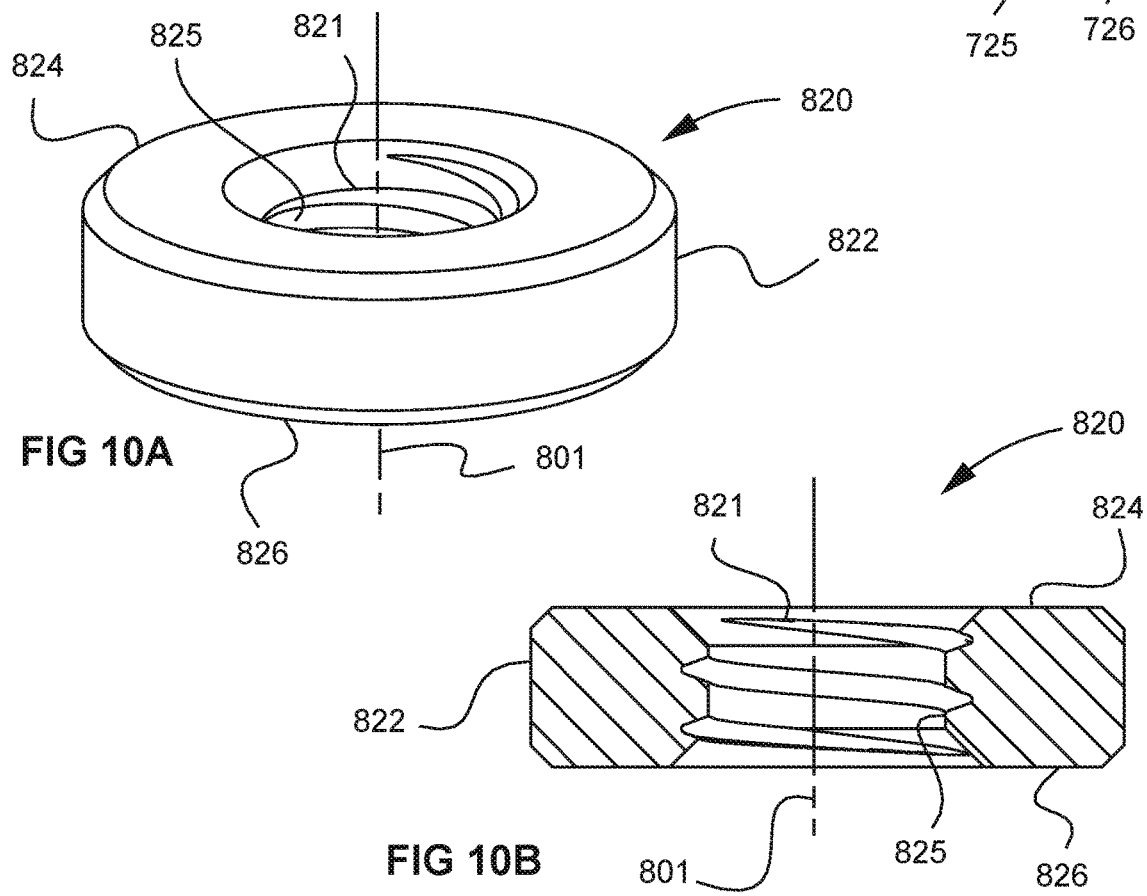

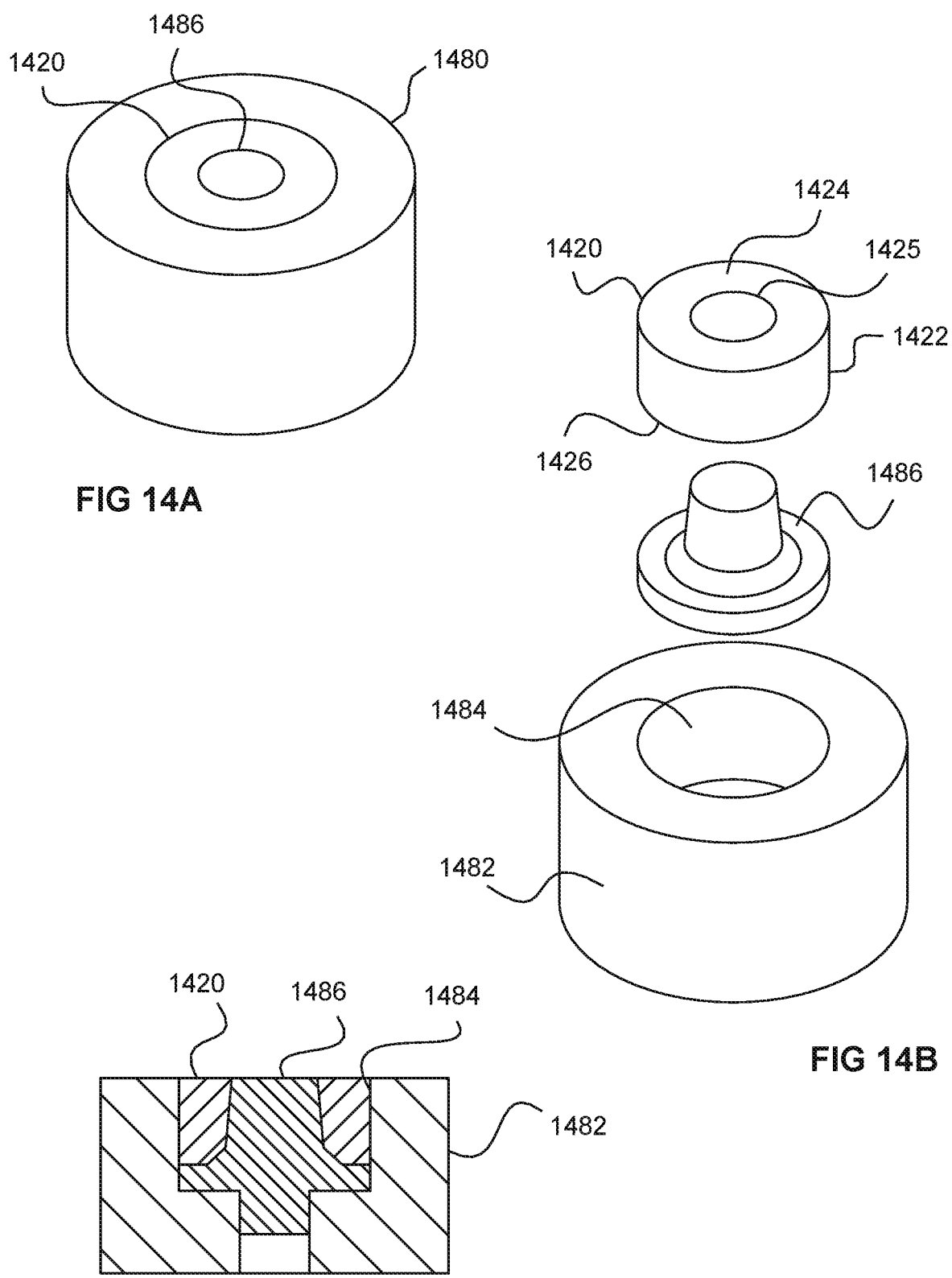

METHODS AND APPARATUS FOR FACILITATING GRAFTING IN SURGICAL PROCEDURES

CROSS REFERENCE TO RELATED APPLICATIONS

This application claims the benefit of U.S. Provisional Patent Application No. 62/808,518, accorded a filing date of Feb. 21, 2019, the entire disclosure of which is hereby incorporated by reference.

FIELD OF THE INVENTION

The present invention relates to methods and apparatus for facilitating grafting in surgical procedures, such as through graft collars.

SUMMARY

Many surgical procedures are done less invasively, such as via smaller incisions, via minimally invasive methodologies, and/or via closed methodologies with the assistance of a scope for visualization or robotic assistance in delicate anatomic areas. When performing such surgical procedures to repair an injury to a biological structure of a patient, a doctor will typically apply a grafting material to serve as a healing scaffold, e.g., to help the patient's body repair itself while a fixation device and/or system carries all or some of the load around the injured area, which was previously carried by the biological structure of the patient. As the body heals, the fixation device carries less of the load around the previously injured area and the biological structure returns to the normal load bearing functionality.

The grafting materials, which may be formed of synthetic and/or biological materials, is used to facilitate integration of the fixation devices and/or systems to the biological structures of the patient. For example, a grafting material formed from human allograft material may be applied to an area in which a non-biological, bone screw, e.g., formed from titanium or other biologically acceptable material, is employed. The grafting material is applied to facilitate bone-to-screw integration, e.g., to facilitate bone growth to the titanium material of the bone screw, after the bone screw has been driven into a skeletal structure of the patient. The integration of the fixation device and/or system to the biological structure of the patient improves the repair of the underlying injury.

Currently, the conventional surgical methodologies require that the application of grafting material takes place during separate and independent surgical steps from the steps directed to the application of the fixation device and/or system. For example, the grafting material may be applied after a bone screw is driven into the skeletal structure of the patient. However, the separate surgical steps for application of the grafting material leads to additional surgical time and/or additional instruments entering the wound, creating increased risk of infection and/or greater potential for the grafting material to be misapplied or misplaced.

The conventional, separate, procedures for application of grafting materials has non-ideal results in certain situations, such as in some minimally invasive spine fusion procedures, where grafting material cannot be applied posteriorly at all. By way of contrast, in the equivalent open spine fusion procedures, grafting material is nearly always applied posteriorly.

In accordance with one or more aspects of the present invention, however, grafting materials are applied at the same time and/or integrated with the application of the fixation devices and/or system. This accomplished via graft collars. Graft collars allow doctors to apply grafting material at the same time that the fixation device and/or system is engaged with the biological structure of the patient. This is done by engagement of the graft collar to the fixation device and/or system as it is being inserted and positioned in the body, such as via gripping, holding, friction fit, interference fit, threading engagement, etc.

Graft collars enable doctors to directly treat conditions, without additional surgical steps to facilitate the integration, in both open and minimally invasive procedures involving bone and soft tissue.

Graft collars may be formed of synthetic and/or biological materials, attach to biological fixation devices and/or systems, and facilitate integration of the fixation devices and/or system to biological structures of patients. For example, a graft collar may be formed from human allograft material, attach to a titanium bone screw, and facilitate bone—titanium integration (e.g., bone growth to the titanium material of the bone screw) after the bone screw is driven into a skeletal structure of a patient. The graft collars may be compressible and/or flowable, which facilitates a shape change during surgery, depending upon the surgical needs.

Since the grafting material of a graft collar is already engaged with the fixation device and/or system, as such is being applied to the hard and soft tissues of the patient, the use of graft collars allow doctors to operate more efficiently, to position the grafting material more accurately, to employ smaller incisions, and to achieve shorter surgical durations.

DESCRIPTION OF THE DRAWINGS

For the purposes of illustration, there are forms shown in the drawings that are presently preferred, it being understood, however, that the invention is not limited to the precise arrangements and instrumentalities shown.

FIG. 4A is a perspective view of a graft collar engaged with a bone screw in accordance with one or more further embodiments herein;

FIG. 4B is a perspective view of the graft collar engaged with the bone screw of FIG. 4A in a disengaged (exploded) view;

FIG. 5A is a perspective view of a graft collar engaged with a bone screw in accordance with one or more further embodiments herein;

FIG. 5B is a perspective view of the graft collar engaged with the bone screw of FIG. 5A in a disengaged (exploded) view;

FIG. 7A is a perspective view of a graft collar in accordance with one or more further embodiments herein;

FIG. 7B is a longitudinal sectional view of the graft collar of FIG. 7A;

FIG. 8A is a perspective view of a graft collar in accordance with one or more further embodiments herein;

FIG. 8B is a longitudinal sectional view of the graft collar of FIG. 8A;

FIG. 9A is a perspective view of a graft collar in accordance with one or more further embodiments herein;

FIG. 9B is a longitudinal sectional view of the graft collar of FIG. 9A;

FIG. 10A is a perspective view of a graft collar in accordance with one or more further embodiments herein;

FIG. 10B is a longitudinal sectional view of the graft collar of FIG. 10A;

FIG. 14A is a perspective view of a graft collar formed in a mold before or during a surgical procedure in accordance with one or more further embodiments herein;

FIG. 14B is a perspective view of the graft collar and mold of FIG. 14A in a disengaged (exploded) view;

FIG. 14C is a longitudinal sectional view of the graft collar and mold of FIG. 14A;

DETAILED DESCRIPTION OF EMBODIMENTS

Figure 1:
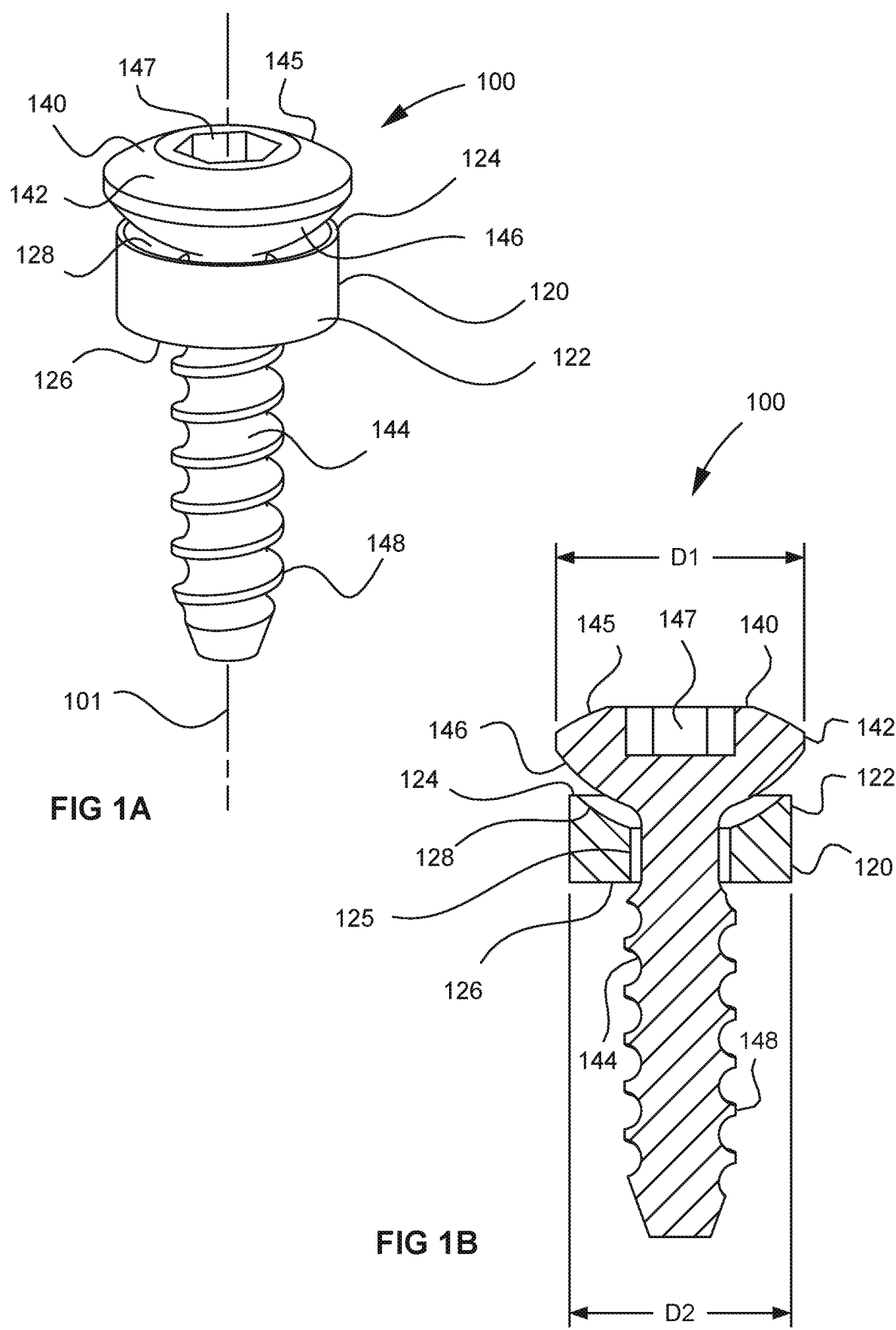
FIG. 1A is a perspective view of a graft collar engaged with a bone screw in accordance with one or more embodiments herein.
FIG. 1B is a longitudinal sectional view of the graft collar engaged with the bone screw of FIG. 1A.

With reference to the drawings wherein like numerals indicate like elements there is shown in FIG. 1A a perspective view of an implant system 100, including a graft collar 120 engaged with a fastener 140 in accordance with one or more embodiments herein. FIG. 1B is a longitudinal sectional view of the implant system 100 of FIG. 1A.

The details of the fastener 140, shown in FIGS. 1A and 1B, exemplify a bone screw and are provided by way of example only, it being understood that the faster 140 may be of many other configurations, such as a bone nail. In the example shown, the fastener 140 includes a head 142 and an elongate body 144, extending along a longitudinal axis 101. The elongate body 144 includes threads 148 to facilitate threaded engagement into a biological structure of the patient, such as one or more bones of the skeletal structure. The head 142 includes a head upper surface 145 and a head lower surface 146, defining a peripheral edge of diameter D1. The head 142 also includes a driver receiver 147 for engagement with a corresponding rotational driver element of an insertion tool. In the example shown, the head lower surface 146 of the fastener 140 is convex and extends from the peripheral edge of the head 142 downward to a shank of the elongate body 144. In this embodiment, the shank of the elongate body 144 is a non-threaded portion extending longitudinally between the lower surface 146 of the head 142 to the beginning of the threads 148.

The details of the graft collar 120, shown in FIGS. 1A and 1B, are provided by way of example only, it being understood that the graft collar 120 may be of many other configurations. In the example shown, the graft collar 120 is of an annular (cylindrical) shape 122, including an upper surface 124 and a spaced apart lower surface 126, defining an outer wall/surface therebetween of diameter D2. The upper surface 124 is characterized by a concavity 128 defining a chamfer or seat extending inwardly into the body of the graft collar 120. The graft collar 120 also includes a longitudinally (axially) extending through hole or bore 125 extending between the upper surface 124 and the lower surface 126.

The specific material from which the graft collar 120 is made will vary based on the surgical procedure and fixation device employed. These materials may include varying degrees of soft and hard cadaveric allografts or synthetic bone void fillers in a variety of formulations to create different levels of shape retention, physical shape change, structural integrity, porosity, and biomaterials with different levels of mineralization to match surgeon preference. Graft collars for spine fusion surgery can be made of human or non-human tissue.

When engaged, the shank of the elongate body 144 of the fastener 140 is located coaxially within the longitudinally (axially) extending through hole or bore 125 of the graft collar 120, such that the graft collar 120 is in alignment with the longitudinal axis 101. By way of example, a diameter of the shank of the elongate body 144 of the fastener 140 is greater than a diameter of the through hole or bore 125. To ensure engagement, however, a diameter between peaks of the threads 148 is larger than the diameter of the through hole or bore 125 of the graft collar 120. As will be discussed in more detail below, the size, shape, and position of the concavity 128 of the graft collar 120 are complementary to the convex characteristics of the head lower surface 146 of the fastener 140, which promotes engagement therebetween.

Figure 2:
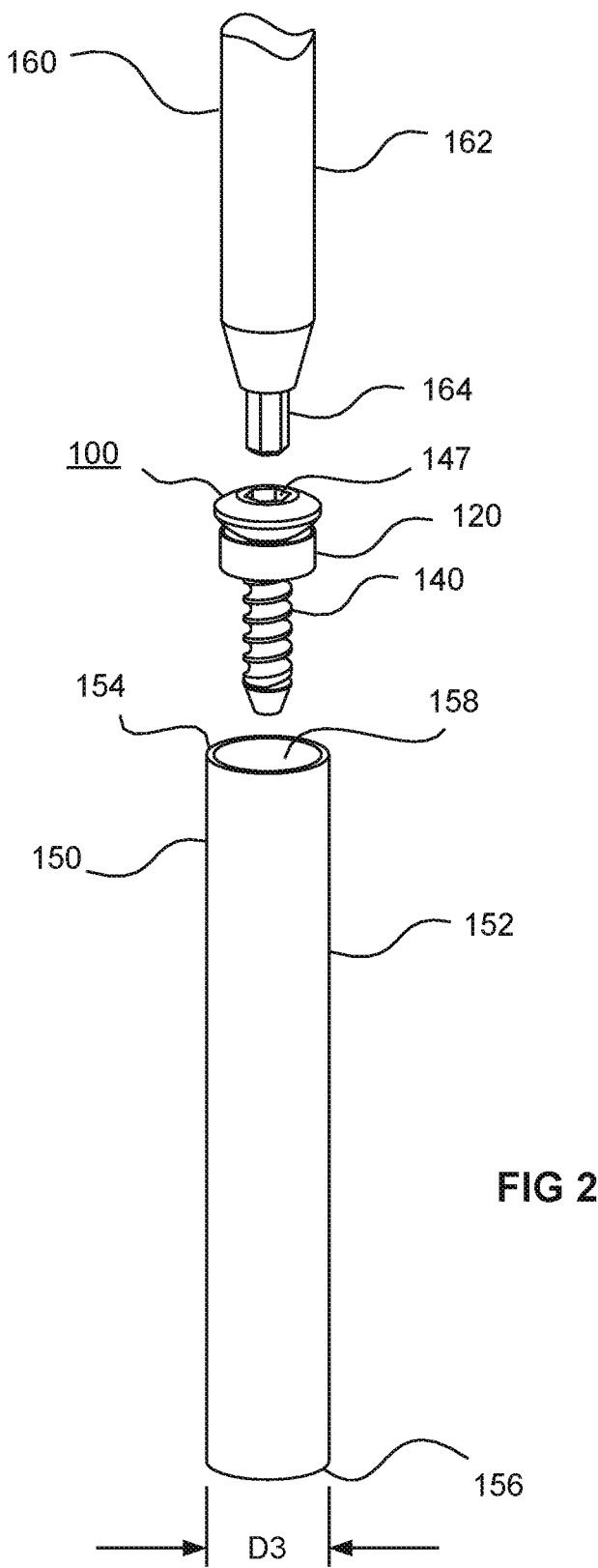
FIG. 2 is a perspective view of an insertion tool and instrument guide arranged to move the graft collar and bone screw of FIG. 1A into position during a surgical procedure.

Further characteristics of the implant system 100 will be discussed with reference to FIGS. 2, 3A, 3B, 3C. As illustrated in FIG. 2, the longitudinal axis 101 of the implant system 100 is aligned with an axis of an instrument guide 150. The instrument guide 150 may be used to extend through an incision through the skin, fat and muscle of the patient to a site where the thread 148 of the elongate body 144 of the fastener 140 is to engage the biological structure, e.g., the bone 110, of the patient. The instrument guide 150 includes a hollow and elongate body 152 extending from a first (proximal) end 154 to a second (distal) end 156. The hollow elongate body 152 defines an internal passage 158 of diameter D3 therethrough.

An insertion tool includes a driver 160 having a longitudinally extending shaft 162, terminating at a drive tip 164. The drive tip is of a complementary size and shape as the driver receiver 147 of the head 142 of the fastener 140. With the drive tip 164 of the insertion tool received within, and engaging, the driver receiver 147 of the head 142, the insertion tool may advance the implant system 100 through the internal passage 158 of the elongate body 152 of the instrument guide 150. Preferably, the diameter D3 is large enough to accommodate the diameters D1 of the head 142 of the fastener 140 and D2 of the graft collar 120. It is noted that the diameter D2 of a graft collar for use in minimally invasive surgery (MIS) of a spine fusion surgery procedure may be smaller than the diameter D1 of the fastener 140 to ensure easy passage down the internal passage 158 of the instrument guide 150. (It is noted that the relatively small diameter D2 of the graft collar 120 may also assists in reducing drag in a tubeless MIS procedure.)

Figure 3A:
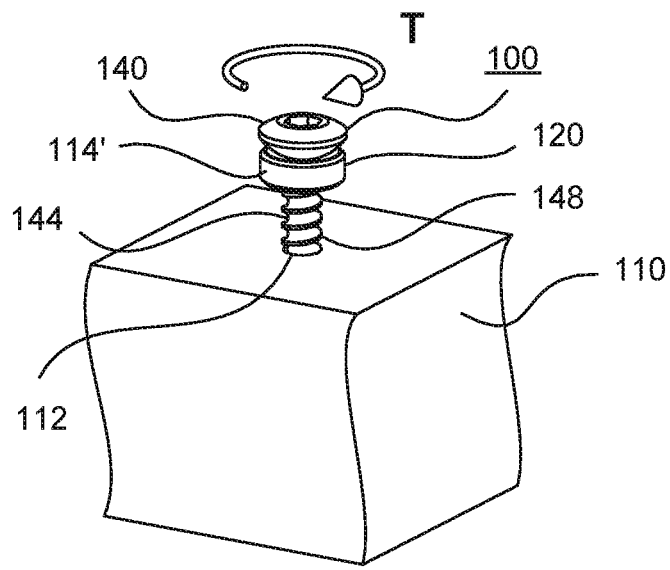
FIGS. 3A, 3B, and 3C are schematic perspective views of the graft collar and bone screw of FIG. 1A as they are driven into a biological structure of a patient during a surgical procedure.

As shown in FIG. 3A, once a tip of the elongate body 144 of the fastener 140 is proximate to a hole 112 in the biological structure, e.g., the bone 110, of the patient, the driver 160, shaft 162, and drive tip 164 of the insertion tool may impart a rotational force to the head 142 of the fastener 140 and set the threads 148 into advancing engagement into the bone 110. As also shown in FIG. 3A, prior to the graft collar 120 engaging the bone 110, the graft collar 120 is characterized by a first shape 114', which includes size, shape, etc. of all aspects thereof. Said another way, the first shape 114' of the graft collar 120 is exhibited at rest, without any eternal forces imparting any elastic deformation thereof.

Figure 3B:
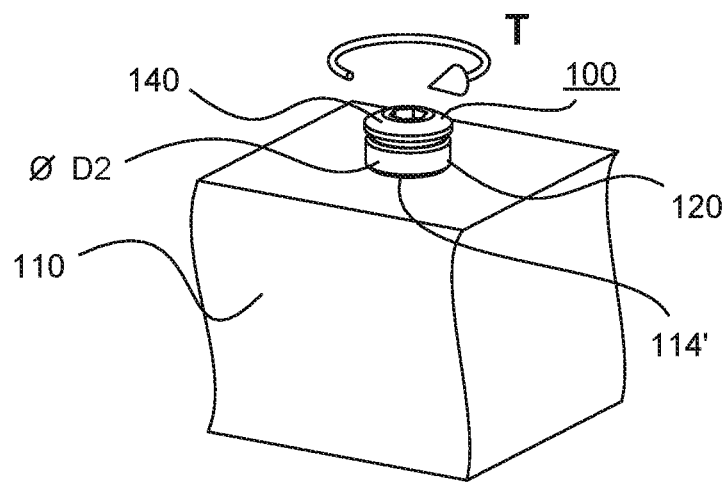
Figure 3C:
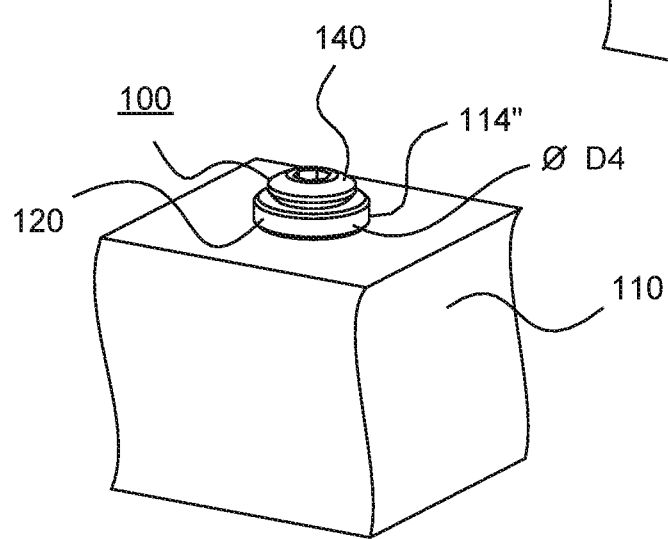

As shown in FIG. 3B, when the insertion tool has advanced the fastener 140 a sufficient amount into the bone 110, the head lower surface 146 of the fastener 140 will engage and press against the concavity 128 of the upper surface 124 of the graft collar 120 from one direction, while the bone 110 will contact the lower surface 126 of the graft collar 120 from another opposite direction. At this point, the graft collar 120 exhibits a diameter Ø D2. As shown in FIG. 3C, when the insertion tool has advanced the fastener 140 even further into the bone 110, the head lower surface 146 of the fastener 140 and the bone 110 elastically deform the graft collar 120 into second shape 114", which includes an increased diameter Ø D4 as compared to diameter Ø D2. It is noted that the body of the graft collar 120 may deform, in response to force from the head lower surface 146 of the fastener 140 during implantation between the condition shown in FIG. 3B and the condition shown in FIG. 3C, such that a change from the first shape 114' to an intermediate shape (not shown) is achieved, which includes an increased diameter of the body as compared to diameter Ø D2.

In one or more embodiments, the material of the graft collar 120 may include characteristics that cause the achieved final, second shape 114" (FIG. 3C) to remain in a relatively solid state, maintaining the achieved compression (elastic deformation) while healing is progressing.

Alternatively and/or additionally, material of the graft collar 120 may include characteristics that permit for wicking of liquid biologics and/or absorption of the patient's blood and cells after the implant system 100 has been deployed (FIG. 3C). The degree of wicking of liquid biologics and/or absorption of the patient's blood and cells may be varied based on a designed porosity and/or relative hydration level of the graft material of the graft collar 120, such as by designing with varying degrees of open areas to retain fluids within the graft material. In the process of wicking, the graft material of the graft collar 120 may expand or shrink, or become independent of the delivery mechanism, depending on desired surgical result.

Alternatively and/or additionally, material of the graft collar 120 may include characteristics that permit a timed phase change or melting to occur, which results in the graft material of the graft collar 120 to flow to a lower fusion site around the fixation device. The specific timing of the phase change from a solid to a gel/liquid during melting may be controlled through graft material design, which ensures the collar graft 120 remains in the first shape 114 during the surgical insertion process (FIGS. 2 and 3A).

Figure 4C:
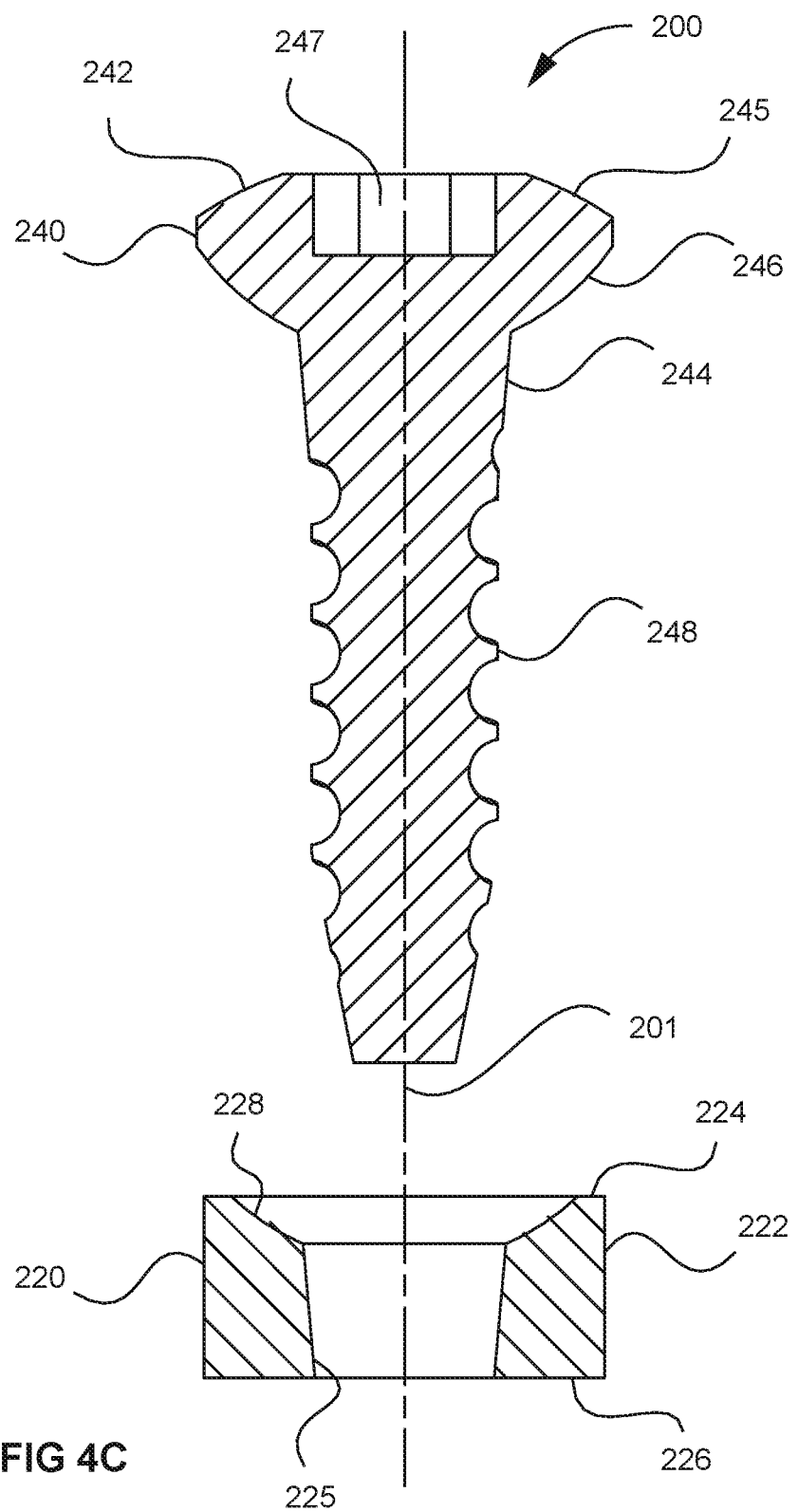
FIG. 4C is a longitudinal sectional view of the graft collar engaged with the bone screw of FIG. 4B.

FIGS. 4A, 4B, and 4C are perspective, exploded, and longitudinal sectional views, of an implant system 200 in accordance with one or more further embodiments. The implant system 200 is similar to the implant system 100, and therefore includes the characteristics, functions, etc., discussed above; however, the implant system 200 also includes one or more variations, which will be discussed below. The implant system 200 includes a graft collar 220 engaged with a fastener 240.

In the example shown, the fastener 240 includes a head 242 and an elongate body 244, extending along a longitudinal axis 201, 421. The elongate body 244 includes threads 248 to facilitate threaded engagement into a biological structure of the patient, such as one or more bones 110 of the skeletal structure. The head 242 includes a head upper surface 245, a head lower surface 246, and a driver receiver 247. In the example shown, the head lower surface 246 of the fastener 240 is convex and extends from the peripheral edge of the head 242 downward to a shank of the elongate body 244. In this embodiment, the shank of the elongate body 244 is a non-threaded portion extending longitudinally between the lower surface 246 of the head 242 to the beginning of the threads 248.

In the example shown, the graft collar 220 is of an annular (cylindrical) shape 222, including an upper surface 224 and a spaced apart lower surface 226, defining an outer wall/surface therebetween. The upper surface 224 is characterized by a concavity 228 defining a chamfer or seat extending inwardly into the body of the graft collar 220. The graft collar 220 also includes a longitudinally (axially) extending through hole or bore 225 extending between the upper surface 224 and the lower surface 226.

As best seen in FIG. 4C, the shank of the elongate body 244 of the fastener 240 is tapered, having a larger diameter at the head lower surface 246 as compared to a diameter of the shank just before the threads 248. In a cooperative manner, the longitudinally (axially) extending through hole or bore 225 of the graft collar 220 is also tapered. In accordance with design consideration, the graft collar 220 may be sized with only one taper or multiple tapers to permit retention on shafts diameters ranging from about 3.00 mm to about 10 mm. Mating tapers may also expand the graft collar 220 (i.e., deform same) into a second shape as compared with a first shape at rest, shown in FIG. 4C.

FIGS. 5A and 5B are perspective and longitudinal sectional views, of an implant system 300 in accordance with one or more further embodiments. The implant system 300 is similar to the implant system 100, and therefore includes the characteristics, functions, etc., discussed above; however, the implant system 300 also includes one or more variations, which will be discussed below. The implant system 300 includes a graft collar 320 engaged with a fastener 340.

In the example shown, the fastener 340 includes a head 342 and an elongate body 344, extending along a longitudinal axis 301. The elongate body 344 includes threads 348 to facilitate threaded engagement into a biological structure of the patient, such as one or more bones 110 of the skeletal structure. The head 342 includes a head upper surface 345, a head lower surface 346, and a driver receiver 347. The graft collar 320 is of an annular (cylindrical) shape 322, including an upper surface 324 and a spaced apart lower surface 326, defining an outer wall/surface therebetween.

As best seen in FIG. 5B, the head lower surface 346 of the fastener 340 is flat (not convex as in previous embodiments) as it extends from the peripheral edge of the head 342 radially inwardly to a shank of the elongate body 344. As in previous embodiments, the shank of the elongate body 344 is a non-threaded portion extending longitudinally between the lower surface 346 of the head 342 to the beginning of the threads 348. The upper surface 324 of the graft collar 320 may be characterized by a flat surface (not concave as in previous embodiments). The graft collar 320 also includes a longitudinally (axially) extending through hole or bore 325 extending between the upper surface 324 and the lower surface 326.

It is noted that in alternative embodiments, the upper surface 324 of the graft collar 320 may alternatively be characterized by a concavity as in the previous embodiments. Additionally and/or alternatively, the shank of the elongate body 344 of the fastener 340 may be tapered (or alternatively straight), with or without a corresponding tapered longitudinally (axially) extending through hole or bore 325 of the graft collar 320.

Figure 6:
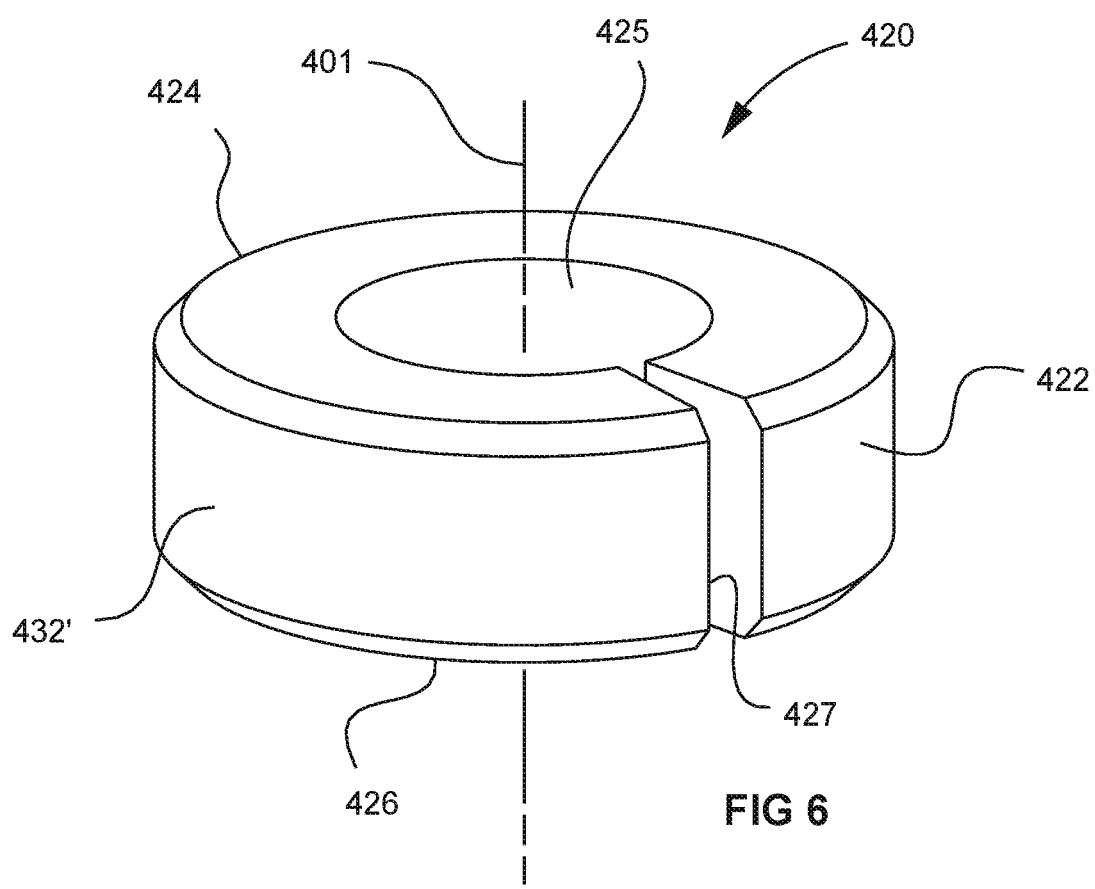
FIG. 6 is a perspective view of a graft collar in accordance with one or more further embodiments herein.

Reference is now made to FIG. 6, which is a perspective view of a graft collar 420 in accordance with one or more further embodiments herein. In the example shown, the graft collar 420 is of an annular (cylindrical) shape 422, including an upper surface 424 and a spaced apart lower surface 426, defining an outer wall/surface therebetween. The graft collar 420 also includes a longitudinally (axially) extending through hole or bore 425, extending along an axis 401, between the upper surface 424 and the lower surface 426. At rest, the graft collar 420 exhibits a shape 432' (without elastic deformation). The graft collar 420 also includes a split or gap 427, which permits some additional functionality when engaging the graft collar 420 with a fastener (e.g., any of the fasteners disclosed herein). The split or gap 427 may serve to accommodate a taper on the fastener, provide material memory (to return to a particular diameter after stretching to go over a larger diameter area such as one of the aforementioned threads 148, 248, 348 or smooth shafts), and/or to create better retention based on the elasticity or flex inherent in the grafting material. The C-shape of the graft collar 420, permits placement and engagement to the fastener from the side of the fastener and/or to add the graft material into an area where a void remains after implantation.

Reference is now made to FIGS. 7A and 7B, which are a perspective, and a longitudinal sectional view, of a graft collar 520 in accordance with one or more further embodiments herein. In the example shown, the graft collar 520 is of an annular (cylindrical) shape 522, including an upper surface 524 and a spaced apart lower surface 526, defining an outer wall/surface therebetween. The graft collar 520 also includes a longitudinally (axially) extending through hole or bore 525, extending along an axis 501, between the upper surface 524 and the lower surface 526. At rest, the graft collar 520 exhibits a shape 532' (without elastic deformation). As best seen in FIG. 7B, the upper surface 524 is not parallel to the lower surface 526, but rather exhibits a particular angle A. The particular angle A may be established to accommodate different boney voids or gaps expected and/or present in the patient's biological structure or provide a desired orientation of a fastener.

Reference is now made to FIGS. 8A and 8B, which are a perspective, and a longitudinal sectional view, of a graft collar 620 in accordance with one or more further embodiments herein. In the example shown, the graft collar 620 is of an non-annular, asymmetrical shape 622, including an upper surface 624 and a spaced apart lower surface 626, defining an outer wall/surface therebetween. The graft collar 620 also includes a longitudinally (axially) extending through hole or bore 625, extending along an axis 601, between the upper surface 624 and the lower surface 626. As best seen in FIG. 8B, the axis 601 is asymmetrically disposed through the graft collar 620, which non-annular, asymmetrical shape 622 allows for a biased placement of the graft material away from the sacrum and/or an adjacent non-fused level of a spinal fusion application.

Reference is now made to FIGS. 9A and 9B, which are a perspective, and a longitudinal sectional view, of a graft collar 720 in accordance with one or more further embodiments herein. In the example shown, the graft collar 720 is of an annular (cylindrical) shape 722, including an upper surface 724 and a spaced apart lower surface 726, defining an outer wall/surface therebetween. The graft collar 720 also includes a longitudinally (axially) extending through hole or bore 725, extending along an axis 701, between the upper surface 724 and the lower surface 726. At rest, the graft collar 720 exhibits a shape 732' (without elastic deformation). As best seen in FIG. 9B, the semi-longitudinally (axially) extending through hole or bore 725 is disposed such that the axis 701 is not perpendicular to the upper surface 724 and the lower surface 726, but rather transverse with respect to perpendicular, see angle B. The angle of the semi-longitudinally (axially) extending through hole or bore 725 may be specifically, directionally oriented in to avoid migration of the graft material to the sacrum and/or an adjacent non-fused level of a spinal fusion application or provide a desired orientation of a fastener.

Reference is now made to FIGS. 10A and 10B, which are a perspective, and a longitudinal sectional view, of a graft collar 820 in accordance with one or more further embodiments herein. In the example shown, the graft collar 820 is of an annular (cylindrical) shape 822, including an upper surface 824 and a spaced apart lower surface 826, defining an outer wall/surface therebetween. The graft collar 820 also includes a longitudinally (axially) extending through hole or bore 825, extending along an axis 801, between the upper surface 824 and the lower surface 826. As best seen in FIG. 10B, the longitudinally (axially) extending through hole or bore 825 includes threads 821, which may engage the threads 148, 248, 348 of the fasteners disclosed herein. This permits an alternative approach to securely engaging the graft collar 820 to the fastener.

Figure 11A:
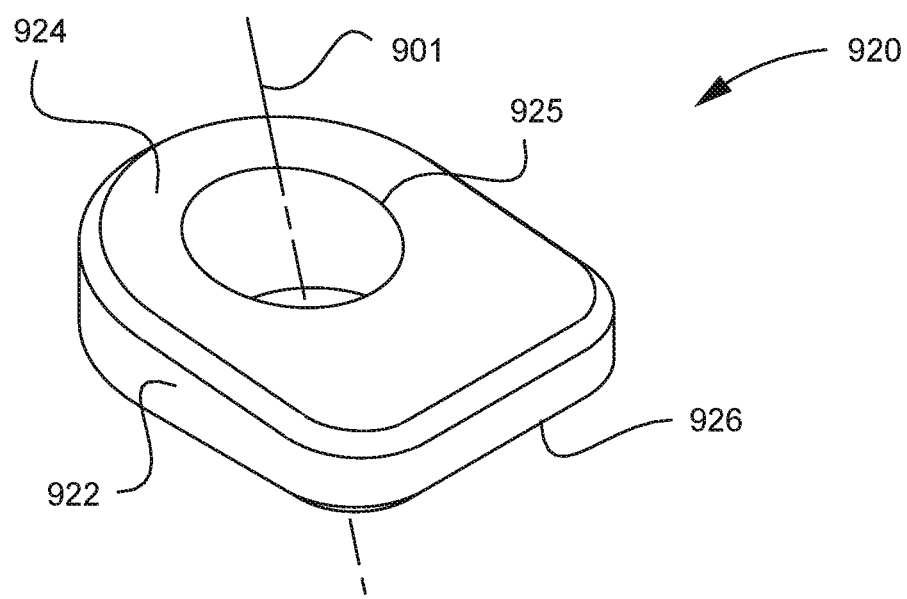
FIG. 11A is a perspective view of a graft collar in accordance with one or more further embodiments herein.
Figure 11B:
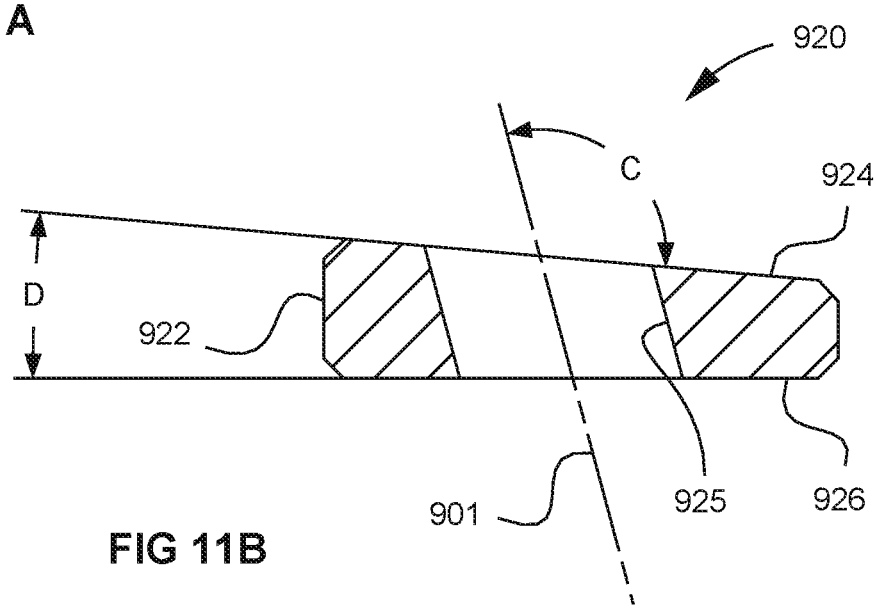
FIG. 11B is a longitudinal sectional view of the graft collar of FIG. 11A.

Reference is now made to FIGS. 11A and 11B, which are a perspective, and a longitudinal sectional view, of a graft collar 920 in accordance with one or more further embodiments herein. In the example shown, the graft collar 920 is of an non-annular, asymmetrical shape 922, including an upper surface 924 and a spaced apart lower surface 926, defining an outer wall/surface therebetween. The graft collar 920 also includes a semi-longitudinally (axially) extending through hole or bore 925, extending along an axis 901, between the upper surface 924 and the lower surface 926. As best seen in FIG. 1B, the upper surface 924 is not parallel to the lower surface 926, but rather exhibits a particular angle D. The particular angle D may be established to accommodate different boney voids or gaps expected and/or present in the patient's biological structures. In addition, the axis 901 is asymmetrically disposed through the graft collar 920, which itself is of a non-annular, asymmetrical shape 922, which allows for a biased placement of the graft material away from the sacrum and/or an adjacent non-fused level of a spinal fusion application. In addition, the semi-longitudinally (axially) extending through hole or bore 925 is disposed such that the axis 901 is not perpendicular to the upper surface 924 and the lower surface 926, but rather transverse with respect to perpendicular, see angle C. The angle of the semi-longitudinally (axially) extending through hole or bore 925 may be specifically, directionally oriented in to avoid migration of the graft material to the sacrum and/or an adjacent non-fused level of a spinal fusion application or provide a desired orientation of the fastener in bone 110.

Figure 12:
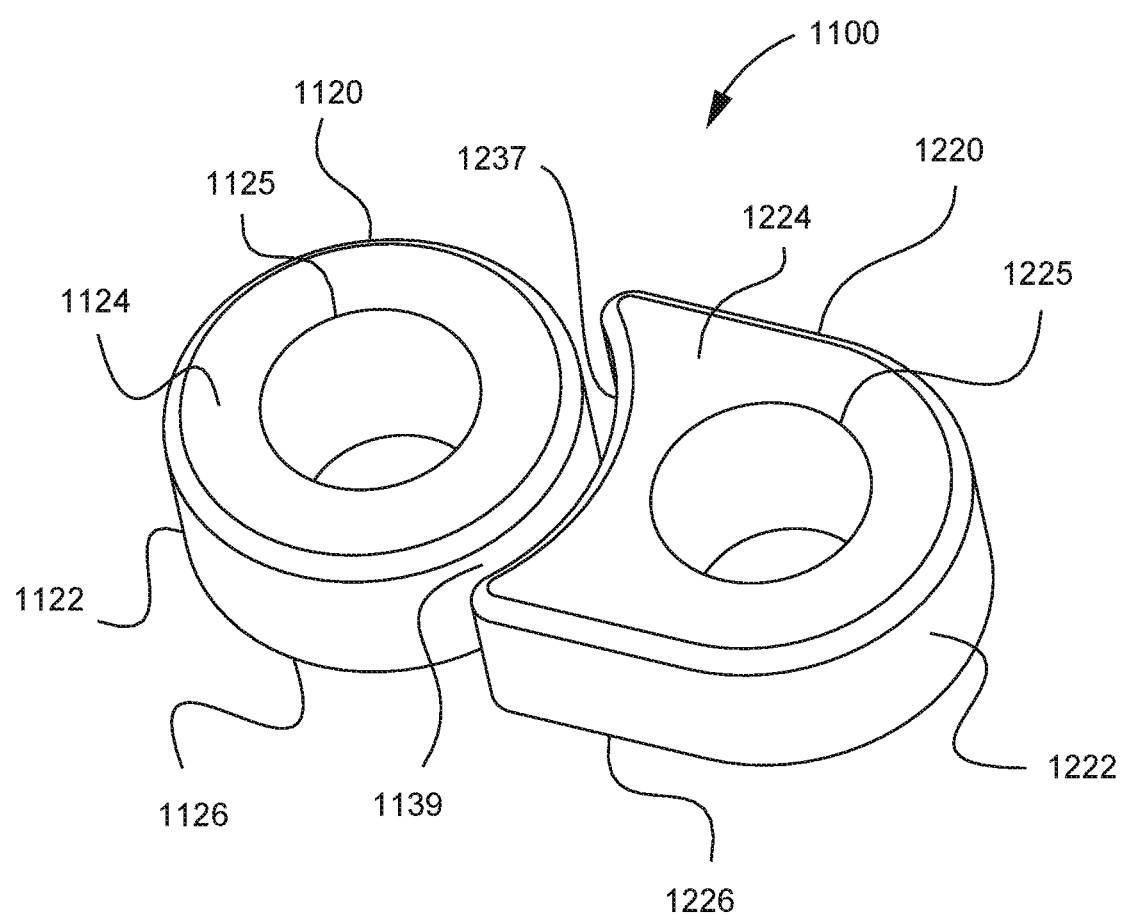
FIG. 12 is a perspective view of nesting graft collars in accordance with one or more further embodiments herein.

Reference is now made to FIG. 12, which is a perspective view of a graft collar system 1100 in accordance with one or more further embodiments herein. In the illustrated example, the graft collar system 1100 includes a first graft collar 1120 and a second graft collar 1220, which are specifically sized and shaped to nest with one another. In the example shown, the first graft collar 1120 is of an annular (cylindrical) shape 1122, including an upper surface 1124 and a spaced apart lower surface 1126, defining an outer wall/surface therebetween. The first graft collar 1120 also includes a longitudinally (axially) extending through hole or bore 1125, extending along a first axis, between the upper surface 1124 and the lower surface 1126. In the example shown, the second graft collar 1220 is of an non-annular, asymmetrical shape 1222, including an upper surface 1224 and a spaced apart lower surface 1226, defining an outer wall/surface therebetween. The second graft collar 1220 also includes a longitudinally (axially) extending through hole or bore 1225, extending along a second axis, between the upper surface 1224 and the lower surface 1226. Notably, the second axis is asymmetrically disposed through the graft collar 1220.

As previously mentioned the first graft collar 1120 and the second graft collar 1220 are specifically sized and shaped to nest with one another, such that they do not overlap one another, yet there shapes enable desired placements of the graft material, including desired distances between the first and second axes of the respective longitudinally (axially) extending through holes or bores 1125, 1225. In particular, the second graft collar 1220 includes a concavity 1237 in the outer wall, which is of a size and shape that corresponds and complements a portion 1139 of the outer wall of the first graft collar 1120, permitting the first and second graft collars 1120, 1220 to nest.

Figure 13:
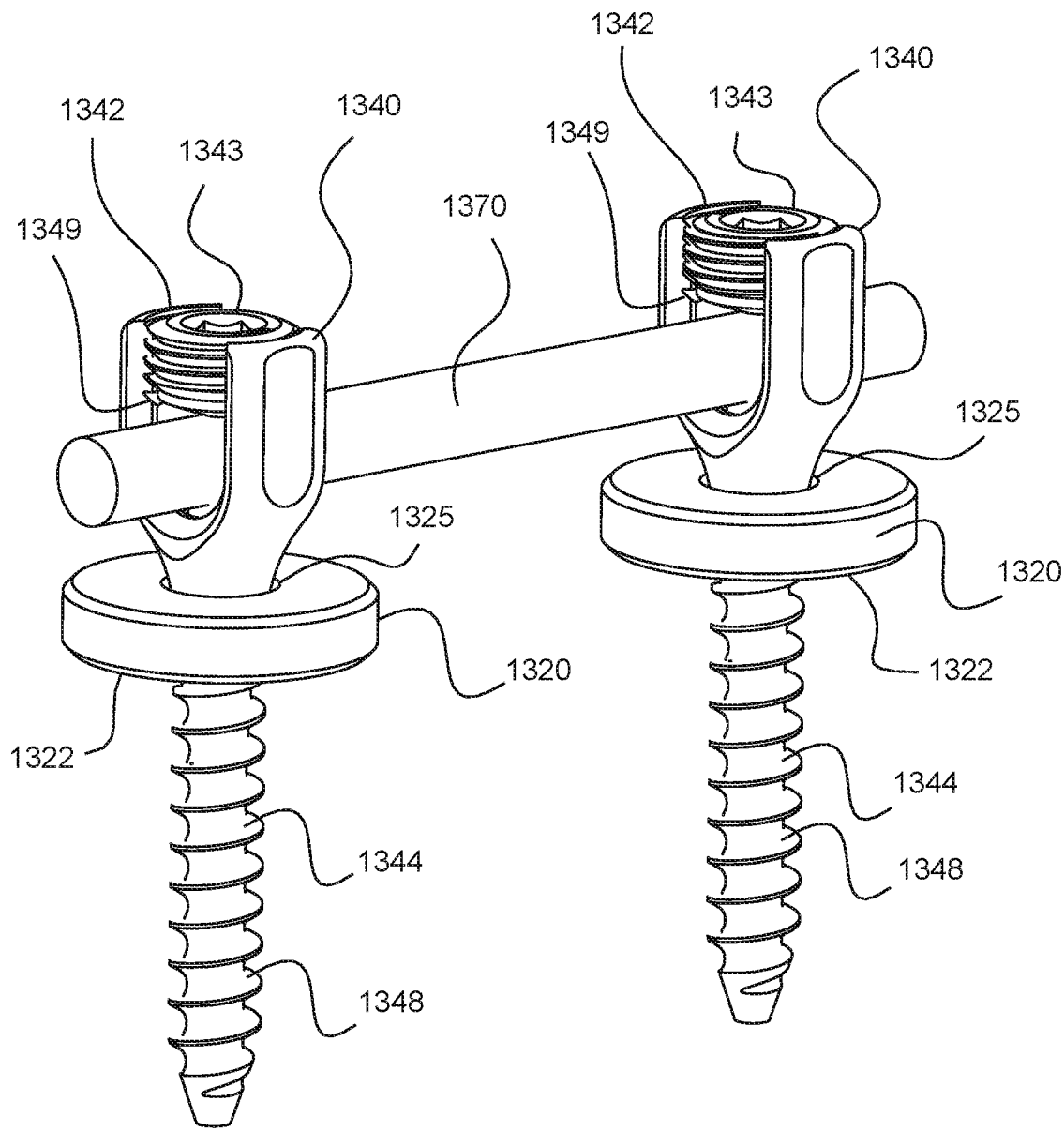
FIG. 13 is a perspective view of a fixation system employing numerous fixation devices, including two bone screws and respective graft collars engaged with each bone screw in accordance with one or more further embodiments herein.

Reference is now made to FIG. 13, which is a perspective view of a system employing a pair of implant systems suitable for use in intervertebral stabilization and/or fusion. Each of the implant systems is similar to one or more of the previously discussed implant systems 100, 200, 300 and therefore includes the characteristics, functions, etc., discussed above. Each of the implant systems includes a graft collar 1320 engaged with a fastener 1340. The specific design of the graft collar 1320 may be in accordance with any of the aforementioned graft collars (and/or combinations of features thereof). In the example shown, the fastener 1340 of each implant system includes a head 1342 and an elongate body 1344, extending along a respective longitudinal axis. The elongate body 1344 includes threads 1348 to facilitate threaded engagement into a biological structure of the patient, such as one or more bones 110 of the skeletal structure. The head 1342 includes a tulip structure 1349 that engages a set screw 1343. In the illustrated example, the graft collar 1320 of each implant system is of an annular (cylindrical) shape 1322, including an upper surface and a spaced apart lower surface, defining an outer wall/surface therebetween. A rod 1370 extends between the respective tulips of the implant systems, and is retained by the respective set screws 1343. When the respective fasteners 1340 of each implant system are driven into the bone 110 of the patient, the graft collars 1320 of each implant system are properly located, elastically deformed, and/or exhibit the various characteristics previously discussed in connection with other embodiments.

Reference is now made to FIGS. 14A, 14B, and 14C, which are a perspective view, a disengaged (exploded) view, and a longitudinal sectional view, respectively of a graft collar 1420 formed in a mold 1480 before or during a surgical procedure in accordance with one or more further embodiments herein. Indeed, some surgeons may desire to form the graft collar 1420 in time proximity to the actual surgical procedure, such as after evaluating the particular characteristics of the injury and/or the patient's physiological characteristics, thereby achieving a particular collar geometry. The surgeon may also control the particular mixture of grafting materials, pre-op or during the surgical procedure.

The mold 1480 includes a base outer mold portion 1482 defining an inner cavity 1484 of particular geometrical characteristics to a void. An inner mold portion (or pin) 1486 fits within the inner cavity 1484 to define additional geometrical characteristics to the void. The specific sub-materials and proportions thereof to produce the grafting material are mixed and then poured into the void of the mold 1480. After a curing period, the graft collar 1420 having the desired material and geometrical properties is achieved.

A skilled artisan will appreciate that a set of outer mold portion(s) 1482 defining and/or inner mold portion(s) 1486 may be made available to achieve any of the geometrical characteristics of the aforementioned graft collar embodiments.

The mold 1480 may be modular to allow the graft collar to be retained around different major/minor diameter screws with varying degree of taper, by inserting a corresponding pin 1486, from among a set of such pins, into a standard (or one of a series of) outer mold portion(s) 1482. The components of the mold(s) 1480 may be formed from a flexible material to allow for easy changes of the shape by pressing to bend in or out different sections of the mold or adding solid materials to block flow of moldable materials.

Figure 15A:
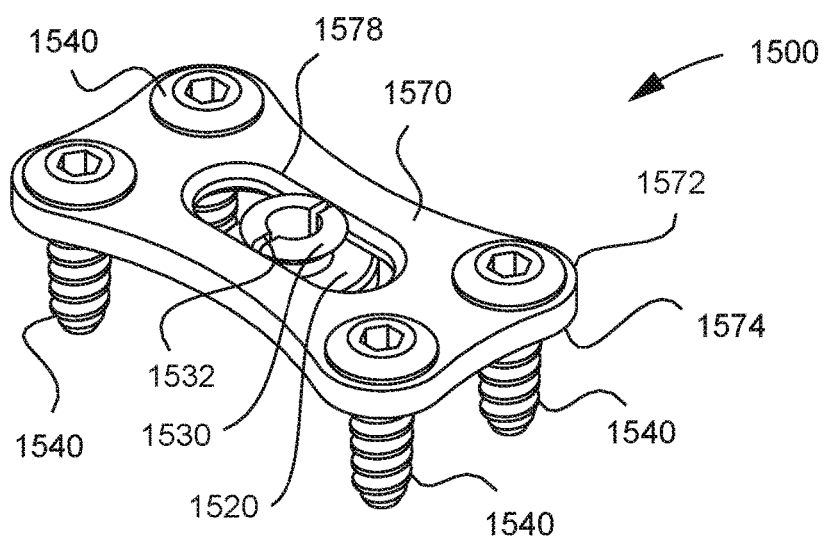
FIG. 15A is a perspective view of a fixation system employing numerous fixation devices, including four bone screws, a bone plate, and a graft collar engaged with the bone plate in accordance with one or more further embodiments herein.
Figure 15B:
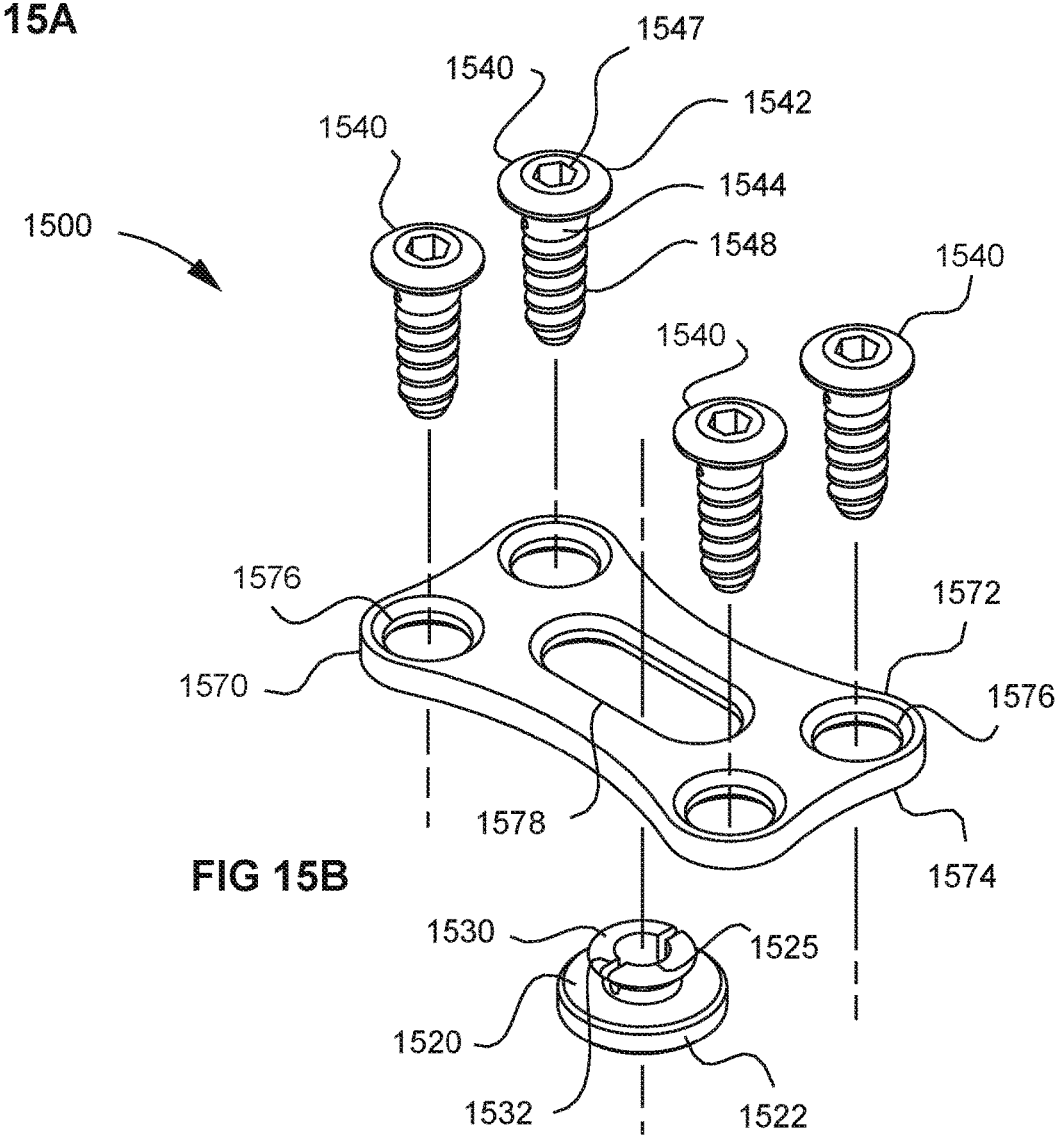
FIG. 15B is a perspective view of the fixation system of FIG. 15A in a disengaged (exploded) view.

Reference is now made to FIGS. 15A and 15B, which are a perspective view and a disengaged (exploded) view, respectively of an implant system 1500 in accordance with one or more further embodiments. The implant system 1500 includes a bone plate 1570 having an upper surface 1572, a spaced apart lower surface 1574, a plurality of apertures 1576, and a centrally disposed aperture 1578. A plurality of fasteners 1540 are used through the plurality of apertures 1576 to engage the bone plate 1570 to one or more bones of a patient's skeletal system (such as to stabilize and/or fuse across an injury, such as an intervertebral injury).

The implant system 1500 also includes a graft collar 1520. In the example shown, the graft collar 1520 is of an annular (cylindrical) shape 1522, including an upper surface and a spaced apart lower surface, defining an outer wall/surface therebetween. The graft collar 1520 also includes a longitudinally (axially) extending through hole or bore 1525, extending along an axis, between the upper surface and the lower surface. The graft collar 1520 includes an annular engagement protrusion 1530 extending from the upper surface. The engagement protrusion 1530 includes slots 1532, which provide some elastic deformation of the engagement protrusion 1530 when inserting same into the centrally disposed aperture 1578 of the bone plate 1570.

Alternatively and/or additionally, one or more of the aforementioned graft collars 120, 220, 320, 420, 520, 620, 720, 820, 920, etc. may be employed on one or more of the fasteners 1540 prior to engagement within one of the apertures 1576. When used with the plate 1570 the graft collars may work internal to the plate slots, ridges or rails with a partial split design incorporating, slight compressibility to allow the grafts to be held in place in open areas around the screws.

Figure 16A:
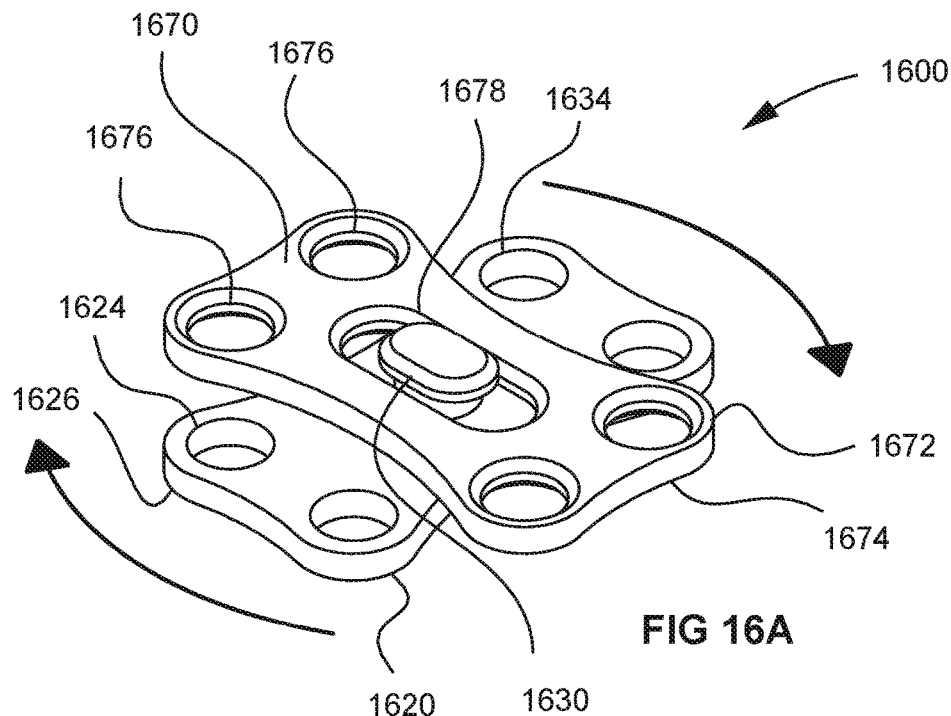
FIG. 16A is a perspective view of a fixation system employing numerous fixation devices, including a bone plate (superior) and a graft collar in plate form (inferior) in an intermediate position of engagement in accordance with one or more further embodiments herein.
Figure 16B:
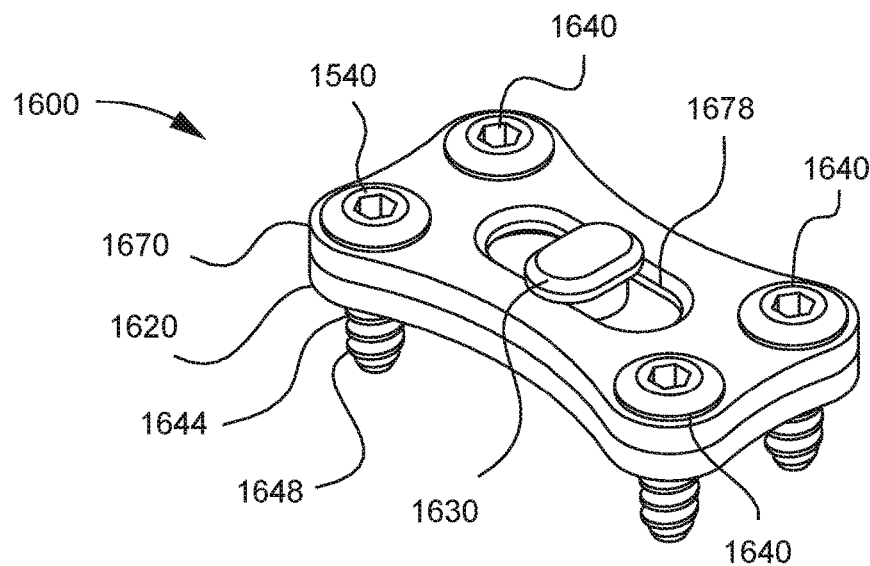
FIG. 16B is a perspective view of the fixation system of FIG. 16A in a fully engaged position, including four bone screws.

Reference is now made to FIGS. 16A and 16B, which are a perspective view and a disengaged (exploded) view, respectively of an implant system 1600 in accordance with one or more further embodiments. The implant system 1600 includes a bone plate 1670 having an upper surface 1672, a spaced apart lower surface 1674, a plurality of apertures 1676, and a centrally disposed, elongate aperture 1678.

The implant system 1600 also includes a graft plate 1620. In the example shown, the graft plate 1620 is of a shape that complements the shape of the bone plate 1670, including an upper surface 1624, a spaced apart lower surface 1626, and a plurality of apertures 1634. The graft plate 1620 also includes an annular engagement protrusion 1630 extending from the upper surface 1624. The engagement protrusion 1630 includes an elongate head on a shank, where the shank extends from the upper surface 1624.

In order to engage the graft plate 1620 to the bone plate 1670, a rotation is established therebetween by some angle (e.g., 90 degrees) so that the elongate head of the engagement protrusion 1630 may enter the centrally disposed, elongate aperture 1678 of the bone plate 1670 from below. Then, a counter-rotation is established therebetween so that the respective pluralities of apertures 1634, 1676 of the graft plate 1620 and the bone plate 1670 are in registration with one another.

A plurality of fasteners 1640 are used through the plurality of apertures 1676, 1634 to engage the bone plate 1670 and the graft plate 1620 to one or more bones of a patient's skeletal system (such as to stabilize and/or fuse across an injury, such as an intervertebral injury).

Alternatively and/or additionally, one or more of the aforementioned graft collars 120, 220, 320, 420, 520, 620, 720, 820, 920, etc. may be employed on one or more of the fasteners 1640 prior to engagement within the apertures 1676, 1634.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A graft collar, comprising:
   a body including an upper surface and a spaced apart lower surface defining an outer wall and surface therebetween;
   an engagement section located on the upper surface of the body sized and shaped to engage a head of a load-bearing bone fastener;
   a substantially planer engagement section on the lower surface to contact a bone surface;
   a through hole extending axially through the body between the upper surface and the lower surface thereof, the through hole being sized to receive therethrough an elongate threaded shank extending from the head of the load-bearing bone fastener,
   wherein the graft collar is non-load bearing and formed from allograft material configured to wick liquids and gradually integrate with bone during healing.

2. The graft collar of claim 1, wherein the engagement section is characterized by a concavity defining a chamfer extending inwardly into the body of the graft collar to engage an a convexly shaped lower surface of the head of the load-bearing bone fastener.

3. The graft collar of claim 1, wherein the engagement section is characterized by a substantially flat surface to engage a substantially flat lower surface of the head of the load-bearing bone fastener.

4. The graft collar of claim 1, wherein a diameter of the head of the load-bearing bone fastener is substantially equal to or less than a diameter of the body of the graft collar.

5. The graft collar of claim 1, wherein the body include a split gap extending from the through hole through to the outer wall and surface.

6. The graft collar of claim 1, wherein the upper and lower surfaces are not parallel, but rather are at an angle with respect to one another.

7. The graft collar of claim 1, wherein an axis of the through hole is asymmetrically disposed through the body of the graft collar, and the outer wall and surface define a non-annular, asymmetrical shape.

8. The graft collar of claim 1, wherein an axis of the through hole is semi-longitudinally extending through the body of the graft collar such that the axis is not perpendicular to the upper surface or the lower surface of the body.

9. The graft collar of claim 1, wherein the through hole is threaded to threadingly engage the threaded shank of the load-bearing bone fastener.

10. The graft collar of claim 1, wherein the material from which the graft collar is formed causes the body to exhibit a first shape at rest, without any eternal forces imparting any elastic deformation thereof.

11. The graft collar of claim 10, wherein the material from which the graft collar is formed causes the body to deform, in response to force from the head of the load-bearing bone fastener during implantation of the load-bearing bone fastener into a patient's bone, from the first shape to an intermediate shape, which includes an increased diameter of the body.

12. The graft collar of claim 11, wherein the material from which the graft collar is formed causes the body to deform, in response to further forces from the head of the load-bearing bone fastener during further implantation of the load-bearing bone fastener into the patient's bone, from the intermediate shape to a final second shape, which includes a further increased diameter of the body.

13. The graft collar of claim 12, wherein the material from which the graft collar is formed causes the final second shape to remain in a relatively solid state, maintaining the achieved elastic deformation while patient healing progresses.

14. The graft collar of claim 1, wherein the material from which the graft collar is formed permits wicking into the graft collar of liquid biologics and/or absorption into the graft collar of a patient's blood and cells after the load-bearing bone fastener and graft collar have been implanted.

15. A system comprising:
   a metal bone fastener having a head, and an elongate threaded shank extending from the head;
   a graft collar having a body including an upper surface and a spaced apart lower surface defining an outer wall and surface therebetween, an engagement section located on the upper surface of the body sized and shaped to engage the head of the metal bone fastener; and a through hole extending axially through the body between the upper surface and the lower surface thereof, the through hole being sized to receive therethrough the elongate threaded shank of the metal bone fastener, wherein the graft collar is non-load bearing and formed from an elastically deformable allograft configured to wick liquids and gradually integrate with bone during healing.

16. The graft collar of claim 1, wherein a diameter of the head of load-bearing bone fastener is larger than a diameter of the body of the graft collar.

17. A graft collar, comprising:

a body including an upper surface and a spaced apart lower surface defining an outer wall and surface therebetween;

an engagement section located on the upper surface of the body sized and shaped to engage a head of a metal bone fastener;

a through hole extending axially through the body between the upper surface and the lower surface thereof, the through hole being sized to receive therethrough an elongate threaded shank extending from the head of the metal bone fastener, wherein the graft collar is formed from a porous allograft with reduced mineralization that is configured to wick liquids and gradually integrate with bone during healing.

18. The graft collar of claim 17, wherein the material from which the graft collar is formed permits wicking into the graft collar of liquid biologics and/or absorption into the graft collar of a patient's blood and cells after the bone fastener and graft collar have been implanted.

19. The graft collar of claim 18, wherein wicking of liquid biologics and/or absorption of a patient's blood and cells causes the graft collar to expand.

\* \* \* \* \*